(12) United States Patent
Newman (10) Patent No.: US 9,453,500 B2
(45) Date of Patent: *Sep. 27, 2016

(54) METHOD AND APPARATUS FOR REMOTE FEATURE MEASUREMENT IN DISTORTED IMAGES

(71) Applicant: DIGITAL WIND SYSTEMS, INC., West Conshohocken, PA (US)

(72) Inventor: John W. Newman, Newtown Square, PA (US)

(73) Assignee: Digital Wind Systems, Inc., West Conshohocken, PA (US)

( * ) Notice: Subject to any disclaimer, the term of this patent is extended or adjusted under 35 U.S.C. 154(b) by 228 days.

This patent is subject to a terminal disclaimer.

(21) Appl. No.: 14/469,292

(22) Filed: Aug. 26, 2014

(65) Prior Publication Data

US 2015/0043769 A1 Feb. 12, 2015

Related U.S. Application Data

(63) Continuation-in-part of application No. 13/839,908, filed on Mar. 15, 2013, now Pat. No. 9,330,449.

(51) Int. Cl.
*H04N 5/33* (2006.01)
*F03D 11/00* (2006.01)
(Continued)

(52) U.S. Cl.
CPC ........... *F03D 11/0091* (2013.01); *F03D 17/00* (2016.05); *G01N 25/72* (2013.01);
(Continued)

(58) Field of Classification Search
CPC ............... G01N 25/72; G06T 2207/10016; G06T 2207/10048; G06T 2207/30164; H04N 5/33
USPC ........................................................ 348/128
See application file for complete search history.

(56) References Cited

U.S. PATENT DOCUMENTS

| 3,371,212 A | 2/1968 | Weiss |
| 3,478,353 A | 11/1969 | Adams, Jr. |

(Continued)

FOREIGN PATENT DOCUMENTS

| EP | 2131037 A2 | 11/2009 |
| EP | 2527649 B1 | 11/2012 |

(Continued)

OTHER PUBLICATIONS

Beattie, A., "Non-Destructive Evaluation of Wind Turbine Blades Using an Infrared Camera", American Institute of Aeronautics and Astronautics, AIAA 99-0046, (1998).*

(Continued)

*Primary Examiner* — Jamie Atala
*Assistant Examiner* — Kathleen Nguyen
(74) *Attorney, Agent, or Firm* — Panitch Schwarze Belisario & Nadel LLP (57) ABSTRACT

A method and apparatus for ground or unmanned aerial vehicle based wind turbine blade inspection consisting of a thermal imaging camera configured to detect the presence of defects by acquiring thermal imaging data from a rotating wind turbine blade when it is not exposed to solar radiation heating and analyzing the thermal imaging data with a processor to identify thermal effects associated with latent defects or damage caused by internal friction due to cyclic gravitational stresses and wind loads during normal turbine operation or aerodynamic cooling of the area around a breach in the blade shell by escaping air, or blockage of residual heat flow or thermoelectric emissions from the rotating blade by the presence of delamination or crushing damage to the blade shell. The system permits latent defects to be identified using a ground-based in situ inspection before they become easily visually apparent, which allowing repairs to be made economically while the blade is in place.

14 Claims, 11 Drawing Sheets

(51) Int. Cl.
  *G01N 25/72* (2006.01)
  *G06T 7/00* (2006.01)
(52) U.S. Cl.
  CPC .... *G06T 7/0004* (2013.01); *F05B 2270/8041* (2013.01); *G06T 2207/10016* (2013.01); *G06T 2207/10048* (2013.01); *G06T 2207/30164* (2013.01); *H04N 5/33* (2013.01); *Y02E 10/722* (2013.01)

(56) References Cited

U.S. PATENT DOCUMENTS

| | | | |
|---|---|---|---|
| 3,810,005 | A | 5/1974 | Bennion et al. |
| 3,922,907 | A | 12/1975 | Hurwitz et al. |
| 4,413,519 | A | 11/1983 | Bannister et al. |
| 4,507,658 | A | 3/1985 | Keating |
| 5,146,289 | A | 9/1992 | Newman |
| 5,257,088 | A | 10/1993 | Tyson, II et al. |
| 5,479,826 | A | 1/1996 | Twerdochlib et al. |
| 5,481,356 | A | 1/1996 | Pouet et al. |
| 5,543,916 | A | 8/1996 | Kachanov |
| 5,748,003 | A | 5/1998 | Zoughi et al. |
| 5,818,242 | A | 10/1998 | Grzybowski et al. |
| 5,923,425 | A | 7/1999 | Dewa et al. |
| 6,153,889 | A | 11/2000 | Jones |
| 6,246,483 | B1 | 6/2001 | Smith et al. |
| 6,366,734 | B1* | 4/2002 | Beran ............... G01C 11/025 348/146 |
| 6,394,646 | B1 | 5/2002 | Ringermacher et al. |
| 6,448,924 | B1 | 9/2002 | Hafer, Jr. |
| 6,674,531 | B2 | 1/2004 | Mähner |
| 6,717,681 | B1 | 4/2004 | Bard et al. |
| 6,881,507 | B2 | 4/2005 | Milacic |
| 6,891,148 | B1 | 5/2005 | Rivera et al. |
| 6,966,754 | B2 | 11/2005 | Wobben |
| 6,968,730 | B2 | 11/2005 | Schafrik et al. |
| 7,019,537 | B2 | 3/2006 | Hazel et al. |
| 7,083,327 | B1 | 8/2006 | Shepard |
| 7,083,384 | B2 | 8/2006 | Bosselmann et al. |
| 7,095,221 | B2 | 8/2006 | Bosselmann et al. |
| 7,283,251 | B1 | 10/2007 | Tansey |
| 7,432,505 | B2 | 10/2008 | Brummel |
| 7,554,324 | B2 | 6/2009 | Gualtieri |
| 7,825,669 | B2 | 11/2010 | Parsons et al. |
| 7,889,119 | B2 | 2/2011 | Evers et al. |
| 8,120,522 | B2 | 2/2012 | Tralshawala et al. |
| 8,174,139 | B1 | 5/2012 | Parsche et al. |
| 8,553,233 | B2 | 10/2013 | Newman |
| 2001/0050772 | A1 | 12/2001 | Meinlschmidt et al. |
| 2004/0236538 | A1 | 11/2004 | Wobben |
| 2005/0157313 | A1 | 7/2005 | Mendlovic et al. |
| 2006/0181285 | A1 | 8/2006 | Friedman et al. |
| 2007/0132461 | A1 | 6/2007 | Holmquist et al. |
| 2008/0237466 | A1 | 10/2008 | Key |
| 2009/0009641 | A1* | 1/2009 | Asayama ............ H03M 1/1014 348/294 |
| 2009/0201364 | A1* | 8/2009 | Konomura ........... G01N 21/954 348/65 |
| 2009/0201971 | A1 | 8/2009 | Goldammer et al. |
| 2010/0103260 | A1* | 4/2010 | Williams ............... F03D 11/00 348/144 |
| 2010/0253569 | A1 | 10/2010 | Stiesdal |
| 2010/0303624 | A1* | 12/2010 | Aderhold ............... F03D 11/00 416/61 |
| 2012/0029840 | A1 | 2/2012 | George |
| 2012/0141275 | A1 | 6/2012 | Hiremath et al. |
| 2012/0253697 | A1 | 10/2012 | Frankenstein et al. |
| 2013/0021471 | A1* | 1/2013 | Waterhouse ............ F24J 2/38 348/139 |
| 2014/0118530 | A1* | 5/2014 | Holmes ................. G01N 25/72 348/92 |
| 2014/0267693 | A1 | 9/2014 | Newman |

FOREIGN PATENT DOCUMENTS

| | | |
|---|---|---|
| GB | 2235604 A | 3/1991 |
| WO | 2007085259 A2 | 8/2007 |
| WO | 2012003372 A2 | 1/2012 |

OTHER PUBLICATIONS

Hung, Y.Y., "Shearography for Non-destructive Evaluation of Composite Structures", Optics and Lasers in Engineering, vol. 24, pp. 161-182, (1996).

Meinlschmidt, P., et al., "Thermographic Inspection of Rotor Blades", ECNDT 2006—Tu.1.5.3 (2006).

Leblanc, B., et al., "Full-Field Inspection of a Wind Turbine Blade Using Three-Dimensional Digital Image Correlation", Industrial and Commercial Applications of Smart Structures Technologies 2011, Proceedings of the SPIE, vol. 7979, pp. 79790L-79790L-12, (Mar. 2011).

Bond, L., et al., "Condition Monitoring Techniques for Composite Wind Turbine Blades", Review of Progress in Quantitative Nondestructive Evaluation, vol. 11B, Proceedings of the 18th Annual Review, Brunswick, ME, Jul. 28-Aug. 2, 1991, pp. 1647-1654 (1992).

Jungert, A., "Damage Detection in Wind Turbine Blades Using Two Different Acoustic Techniques", NDT.net—The e-Journal of Nondestructive Testing (Dec. 2008).

Beattie, A., "Non-Destructive Evaluation of Wind Turbine Blades Using an Infrared Camera", American Institute of Aeronautics and Astronautics, AIAA 90-0046, (1998).

Renshaw, J., et al., The Sources of Heat Generation in Vibrothermography. NDT & E International, vol. 44, Issue 8, pp. 736-739 (Dec. 2011).

Rumsey, M., et al. "Structural Health Monitoring of Wind Turbine Blades".Smart Sensor Phenomena, Technology, Networks, and Systems 2008. Proceedings of the SPIE, vol. 6933, article id. 69330E (2008).

Zell, H., et al., "Wind Turbine Inspection—New Methods of Remote Non-destructive Inspection of Rotorblades", Dewi Magazin No. 40, pp. 14-22 (Feb. 2012).

Anjar, B., et al., "Feasibility Study of Thermal Condition Monitoring and Condition based Maintenance in Wind Turbines", Elforsk Electricity and Power Production, Elforsk rapport 11:19, pp. 1-26 (May 2011).

Rumsey, M., "NDT, CM and SHM of Wind Turbine Blades at the National Labs", 2009 NREL Wind Turbine Condition Monitoring Workshop, Wind and Water Power Technology Laboratories, Albuquerque, NM, (Oct. 2009).

Hyers, R., et al., "Condition Monitoring and Prognosis of Utility Scale Wind Turbines", Energy Materials, vol. 1, No. 3, pp. 187-203 (Sep. 2006).

International Search Report and Written Opinion dated Jul. 8, 2014 for corresponding PCT/US2014/030328 filed Mar. 17, 2014.

Office Action issued May 21, 2015 in U.S. Appl. No. 13/839,908 by Newman.

Office Action issued Oct. 15, 2015 in U.S. Appl. No. 13/839,908 by Newman.

* cited by examiner

METHOD AND APPARATUS FOR REMOTE FEATURE MEASUREMENT IN DISTORTED IMAGES

INCORPORATIONS BY REFERENCE

Applicant hereby incorporates by reference, as if set forth fully herein, the entirety of the disclosures of U.S. Nonprovisional patent application Ser. No. 13/731,085, filed Dec. 30, 2012, now U.S. Pat. No. 8,553,233, and having the title METHOD AND APPARATUS FOR THE REMOTE NONDESTRUCTIVE EVALUATION OF AN OBJECT, U.S. Nonprovisional patent application Ser. No. 13/837,145 filed on Mar. 15, 2013 and having the title METHOD AND APPARATUS FOR MONITORING WIND TURBINE BLADES DURING OPERATION, U.S. Nonprovisional patent application Ser. No. 13/839,908 filed on Mar. 15, 2013 and having the title SYSTEM AND METHOD FOR GROUND BASED INSPECTION OF WIND TURBINE BLADES, and U.S. Nonprovisional patent application Ser. No. 13/840,470, filed on Mar. 15, 2013 and having the title NONDESTRUCTIVE ACOUSTIC DOPPLER TESTING OF WIND TURBINES BLADES FROM THE GROUND DURING OPERATION.

PRIORITY CLAIM

This is a Continuation-in-Part of U.S. Nonprovisional patent application Ser. No. 13/839,908 filed on Mar. 15, 2013, having the title SYSTEM AND METHOD FOR GROUND BASED INSPECTION OF WIND TURBINE BLADES.

BACKGROUND OF THE INVENTION

1. Field of the Invention

This invention relates to a method and apparatus for remotely measuring features in geometrically distorted images, in particular digital photographic and thermal images of wind turbine blades. The invention facilitates such inspections from the ground, on operating wind turbine generators and has utility for remotely detecting propagating latent defects, existing damage and broken adhesive bonds within the skin of a wind turbine blade. This permits subsurface defects to be detected before they become too large for repair in situ, which provides significant economic advantages, as the cost of repairing the wind turbine blade in situ is typically 10% of the cost of replacing a blade.

2. Description of the Related Technology

Due to their large size, extensive surface area and complex shape, wind turbine blades are difficult to non-destructively inspect even within a fabrication or repair facility. Visual inspection cannot identify defects below the surface of the outer skin of the wind turbine blade, which typically is fabricated from a fiberglass material. Active thermography inspection techniques using heat are effective for near surface defects but can give false positives and false negatives due to variations in material thickness and surface emissivity.

Shearography with either thermal stress or during flexure testing of the blade in the factory can be used to detect fiberwaves in spar caps and other areas of the blade, but the technique is slow, expensive and is usually performed only if known issues are suspected. Angle beam ultrasonic techniques are very slow and may not work through thick carbon fiber spar caps.

As a result, blades are commonly installed on towers and put into service with a significant probability of latent manufacturing defects. Furthermore, composite blades are subject to extreme temperature variations. Entrapped water in blades can undergo freeze/thaw cycles, which can cause internal damage. Cyclic forces of gravity and varying forces from the wind acting on the blades as they rotate can cause fatigue damage or the propagation of latent defects over time while manufacturing process mistakes can lead to early blade failure. Defects can grow below the surface of a wind turbine blade to the point that by the time cracks and damage breach the surface and can be detected visually, the damage may not be repairable on tower.

Detecting progressive subsurface damage and propagating defects in wind turbine blades in situ is difficult for a number of different reasons. Inspectors using sky cranes or rope access are expensive, time consuming and put personnel in a very dangerous working environment. While on tower, close access allows inspectors to visually detect blade defects such as trailing edge splits, cracks, lightning damage and blade erosion. In addition, major subsurface delaminations, cracks and debonded adhesive joints can easily go undetected with current technology.

Access to a wind turbine blade in situ with portable instruments for nondestructive testing also requires rope access or sky platforms and cranes. Blade and tower crawlers with nondestructive testing sensors for in situ inspection have been developed and tested, but they can be prohibitively expensive, slow to operate, require repair and maintenance themselves. Their effectiveness is also questionable. Thermal imaging of blades using solar heating during the transition from day to night has been attempted but is very limited in both the time over-which data may be taken and by being limited to blades facing the sun. Further this technique requires stopping the rotors, with consequential loss of revenue.

Helicopter access is both expensive and dangerous in wind farms, and no means are included to quantitatively measure or locate indications. Thermal imaging of blades using solar heating during the transition from day to night is very limited by both the time over-which data may be taken and by being limited to blades facing the sun. Finally, it is common practice to use optical and digital photographic imaging of blades in an attempt to detect visible damage from the ground. Again these methods suffer from complex logistics, insensitivity to defects, poor repeatability and do not allow precise measurement of the defect size, area or the location.

There accordingly exists a need for a fast, cost effective nondestructive inspection system and method for wind turbine blades using digital imaging to detect latent and propagating damage, which includes a method and apparatus for precision measurement of features or anomalies and locating these on the target blade.

SUMMARY OF THE INVENTION

Accordingly, it is an object of the invention to provide analysis of thermal and digital photographic images of turbine blade surfaces for a fast cost effective nondestructive inspection system and method for wind turbine blades to detect latent and propagating damage early enough to allow on-tower repair before it becomes necessary to remove the wind turbine blade from the tower and repair it off-site or replace it with a new blade. The sizing and location of anomalies can be used to classify blade status to provide a useful definition of actions needed to maintain safe turbine operation.

In accordance with the embodiment described herein, a system for inspecting utility scale wind turbine generator blades from the ground for propagating subsurface anomalies during normal operation, comprised of a camera sensitive to the thermal emissions from friction caused by defects subjected to cyclic strain from gravity and wind loading as well as surface or aerodynamically cooled near-surface damage that block thermoelastic emissions from the blade or defect breaches in the blade shell cooled by airflow from pressurized air from within the blade and a means to process thermal images of these anomalies to determine location, signal to noise ratio, size or other quantitative measurements such early detection may allow repair of the blade up tower instead of more costly replacement.

These and various other advantages and features of novelty that characterize the invention are pointed out with particularity in the claims annexed hereto and forming a part hereof However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF PREFERRED EMBODIMENT(S)

Figure 1:
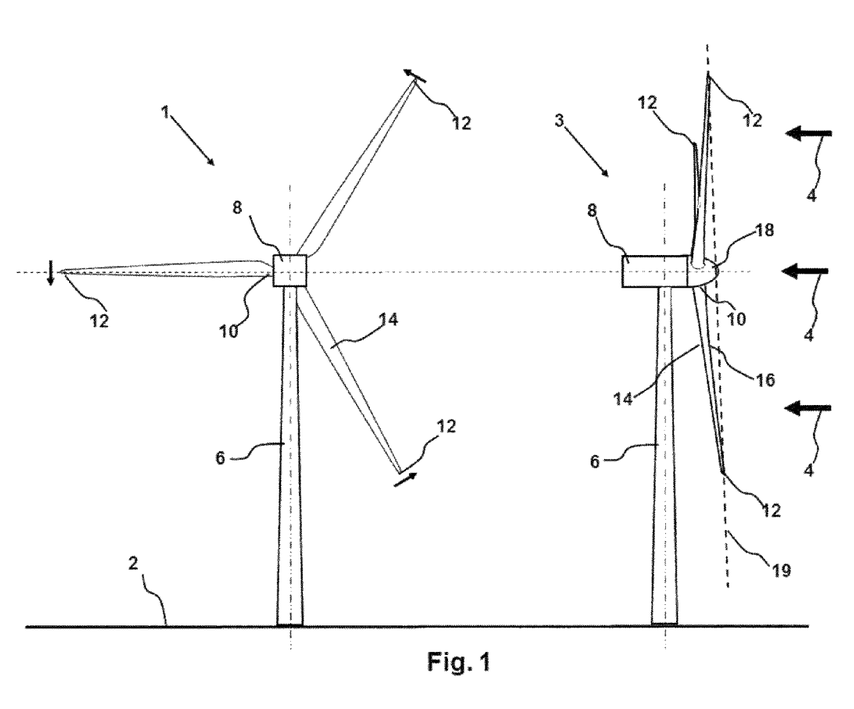
FIG. 1 is a schematic representation of a utility scale, horizontal axis, wind turbine generator.

Referring now to the drawings, wherein like reference numerals indicate corresponding structure throughout, and referring in particular to FIG. 1, a schematic diagram of a HAWT is shown that that is typical of both land based and off-shore turbine generators. The view 1 from behind the turbine facing the wind includes tower 6 extending up from the ground or ocean surface 2 to support the nacelle 8 which contains the generator and gear reducers, unless it is a direct drive generator. There are typically three blades on a utility scale wind turbine having root ends 10 and blade tips 21. As seen from the side view 2, the blade root ends attach to the rotatable hub 18. Blade side 16 facing the wind 4 is often referred to as the high pressure side. The blade side 14, facing away from the wind is referred to as the low pressure or suction side. As the blade speed increases the blade pitch is adjusted to the optimal angle of attack to the wind to create the maximum lift and torque required to drive the electricity generator.

Figure 2:
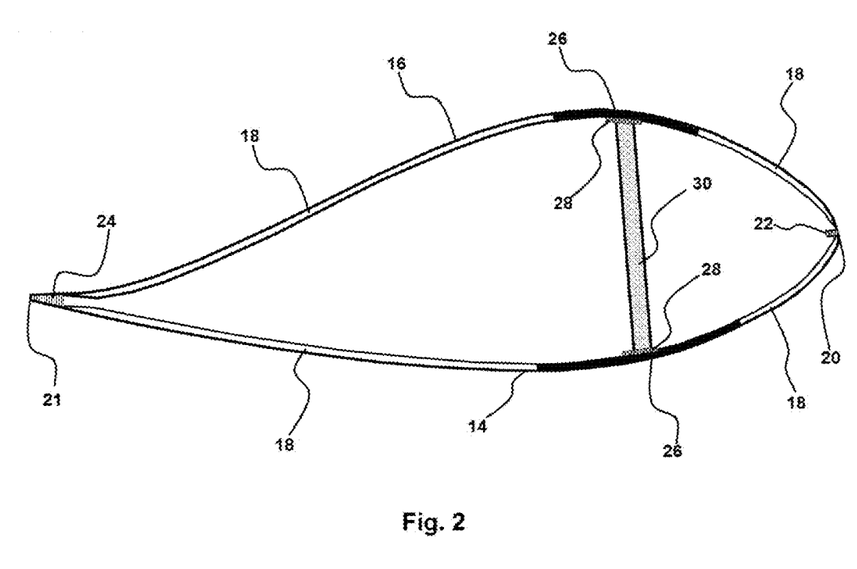
FIG. 2 is a schematic representation of a wind turbine blade cross section.

FIG. 2 shows the construction cross section of a typical HAWT blade. Wind turbine blades are generally manufactured with adhesively bonded composite shells forming the high pressure side 16 and the low pressure side 14. The trailing edge 21 is adhesively bonded as is the leading edge 20, with adhesive bonding in some cases between two flanges 22 formed by the inner and outer fiberglass skins that make up sandwich panels 18. Two spar caps 26, which may be made from fiberglass or carbon fiber laminate are bonded to the edges of the sandwich panels 18. The blade spar web 30, which can be a solid fiberglass laminate or a sandwich construction with fiberglass or carbon fiber face sheets and a core material made with foam, balsa wood or other suitable material with high compressive strength. The spar web 30 is bonded with adhesive 28 to the spar caps 26 to form an I beam. Sometimes a second or even third spar web is present forming a box beam.

Defects such as adhesive disbonds or unbonds present at the spar cap 26 to spar web 30 adhesive bond 28 may lead to catastrophic failure of the blade in service. Fiber waves in the solid spar cap 26 laminate can also lead to cracking and ultimately to blade failure. Further, trailing edge 21 splits or cracks in the high pressure 16 and low 14 pressure side shell adhesive bond 24 may be signs or excessive blade flex during operation. The trailing edge 21 adhesive bond 24, in the area of greatest blade chord width towards the root end 10 supports blade twist loads. Cracks and breaks in the adhesive bond 24 at these locations can also lead to blade failure unless detected in time and the turbine shut down and promptly repaired. When one of the reinforcing elements such as a glass or carbon fiber breaks, it makes a distinct sound, like a stick breaking The sound propagates throughout the structure of the wind turbine blade, and throughout the enclosed space defined by the interior surface of the outer skin of the blade. In addition, a pressure gradient develops within the enclosed space as a result of centripetal acceleration. The pressure differential between the portion of the enclosed space that is proximate the wind turbine hub and the outermost portion of the enclosed space can be on the order of 2 psi.

Figure 3:
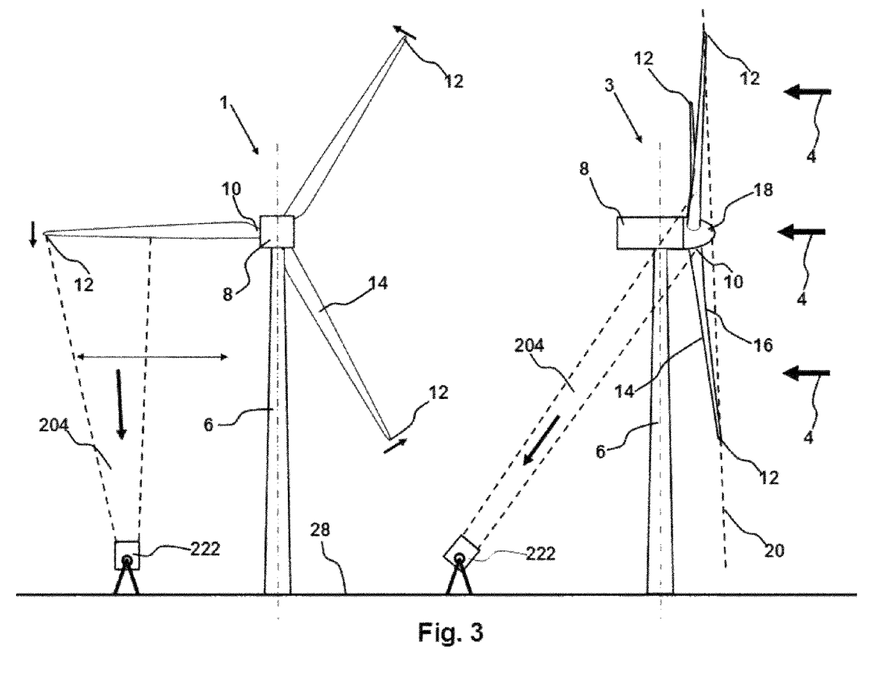
FIG. 3 is a schematic diagram showing the relative location of a thermal camera for inspecting the wind turbine blades that are oriented so as to be substantially perpendicular with respect to the ground or sea level.

FIG. 3 is a schematic diagram showing the side view of thermal camera 222 at locations down wind of tower 6 for inspection of the low pressure side of the blade 11. Thermal emissions 204 from defects in the blade 11 propagating due to cyclic stress load due to gravity and wind fluctuations are detected by thermal camera 222. The side view also shows the plane 20 as a line extending to the ground or sea level 28, containing the blade tips 12. This approximate location is a good viewing position for blade 11 leading edge 20 inspections.

Figure 4:
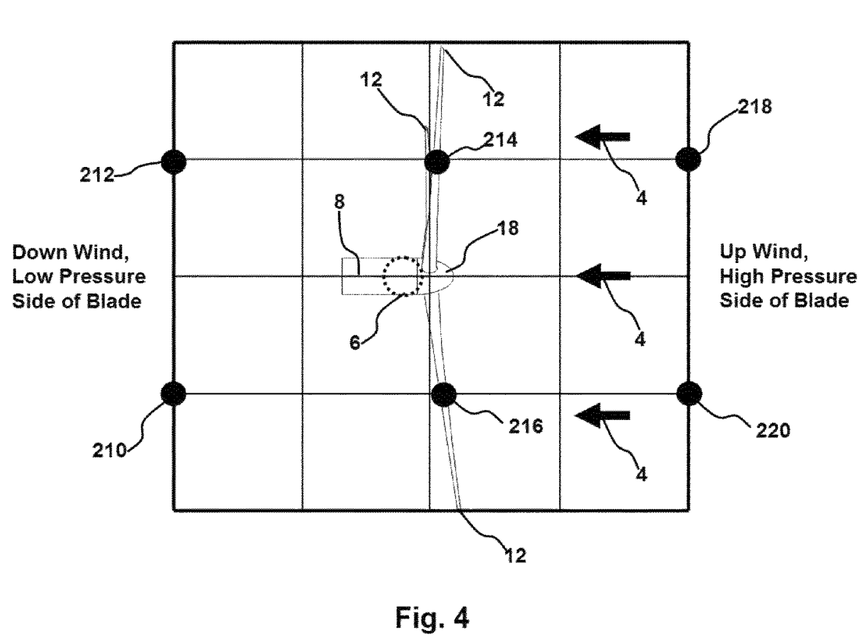
FIG. 4 is a diagrammatical plan view of a wind turbine site with an indication of six placement locations for the thermal camera to view various locations on the blades.

FIG. 4 shows thermal camera 222, positioned at locations both on the up wind-high pressure side of the turbine blades, at two locations on either side of the tower in the plane of the blade disk and at a location on the down wind, low pressure or suction side of the blades to provide advantageous viewing of the entire blade surfaces during rotation. For the best view angle of the low pressure side 14 of the blades 11 is achieved with the thermal camera 222 positioned at approximately location 212, however the best results are obtained using an image stabilizer as described here in or an image peak storage unit or software due to the relatively high speed the image of the blade passes through the camera field of view. The best view of the blade leading edges 20 are at position 214, in the plane 20 of the blade tips, since the blade 11 is rotating down directly at the camera and the angles of points on the leading edge 20 are changing relatively slowly.

Moving down wind from position 214 gives good views of the forward low pressure side surfaces 14, of the blade 11 with relatively low rate of angle changes over three to four video frames. Position 216 is excellent for the trailing edge 21 of the blades and position 220 offers a full view of the high pressure side 16 of the blade 11, which is best viewed with the image stabilizer or peak storage embodiment described herein. Position 210 offers relatively poor views the low pressure side except for the trailing edge 21 and the aft low pressure sandwich structure 18, but with fast moving angle changes and with the blade twist. Wind turbine farms are often located on hills or mountain ridges with little room to move away from the tower 6. Local conditions and land shapes often dictate where the best viewing angles can be obtained.

Figure 5:
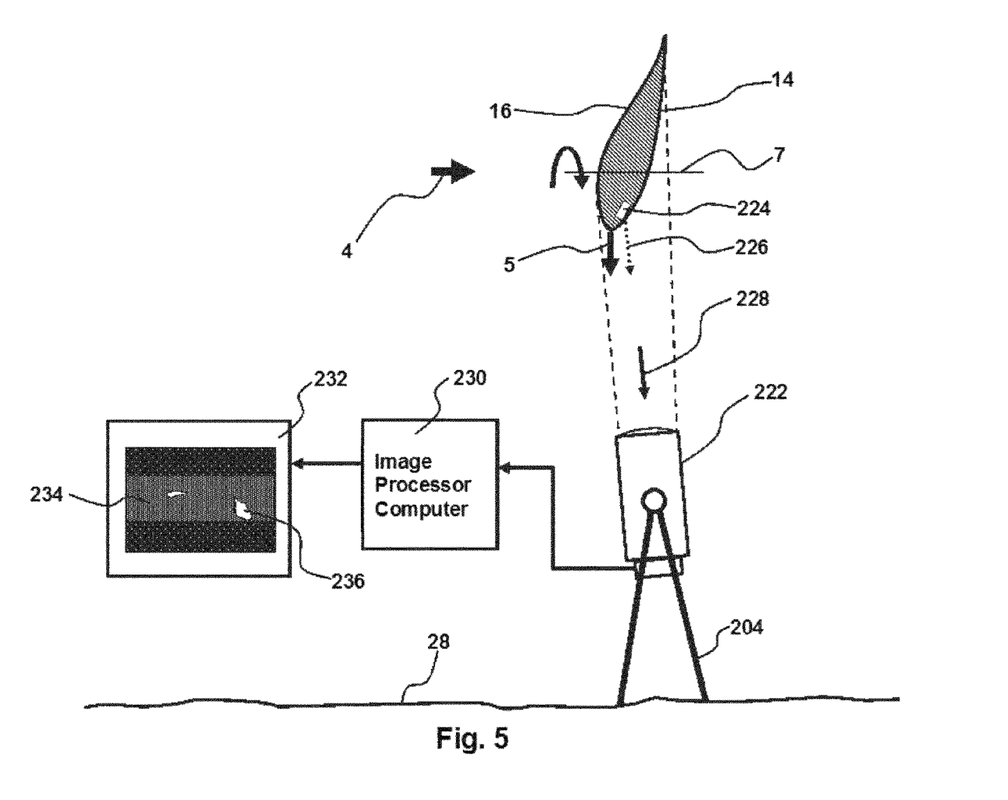
FIG. 5 shows a basic thermal system including an image processing computer that is suitable for direct viewing and recording blade surfaces in or near a wind turbine site.

FIG. 5 is a schematic diagram showing a thermal camera 222, positioned to receive low level thermal radiation 228 from the blade 11 due to thermoelastic emission from the stresses acting on the blade material due to gravitational forces from the blade rotation motion 17.

Emission 226 from the mechanically stressed defect 224 appears warmer in the image produced by thermal camera 222 due to internal friction and plasticity around defect 224.

The camera 222 is positioned under the blade at position 214 to receive thermal radiation 228 from the leading edge and the forward part of the low pressure side 14. This position reduces the angular changes due to blade rotation in the image during the frame acquisition. The streamed video images from the thermal camera 222 are recorded by Image Processing computer 230, or in a memory device in the thermal camera 222 as video files, and processed presented using peak store or other image processing techniques and presented on monitor 232. Various means of processing the images including video image peak store, frame by frame analysis, histogram normalization, unsharp filters and so on to obtain good image quality and quantitative measurements of size and location comparing features of known size at the range to the target.

Figure 6:
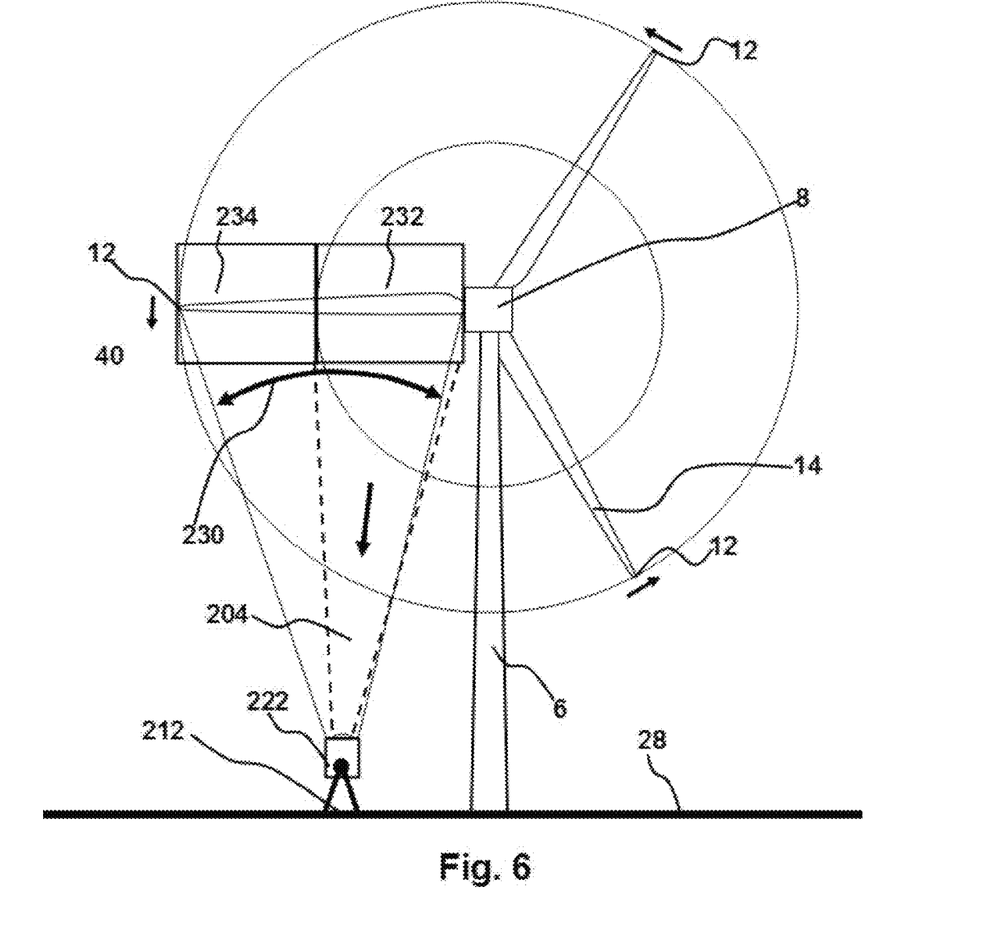
FIG. 6 a schematic showing the thermal camera viewing a low pressure, or suction side of a blade in the horizontal position.

FIG. 6 shows how a thermal camera located at position 212 can be used to test the entire blade from one location by pointing to a blade section inboard adjacent to the generator nacelle 8 and acquiring the thermal image sequences. Moving or rotating the camera in an arc 230 outboard and overlapping the next blade section and so on until the tip is reached. The use of programmed servo or other motor drives to move the camera would allow for a fast automated test.

The preferred embodiment for this method of remotely inspecting a land or offshore wind turbine blade or blades uses a sensitive IR camera with a fast integration time, wherein a single image or a continuous series of images of each blade is recorded as it passes through the field of view of the thermal camera. The IR camera integration time, t, should be fast enough to reduce the degrading effects of blade rotation creating an image without apparent motion smearing at the blade tip, ranging from 0.001 to 100 milliseconds but ideally, t seconds=$\tau/\pi D$, where D is the diameter of the turbine rotor and $\tau$ is the rotation period of the rotor in seconds.

The camera should be sensitive to mid-wave or long wave IR radiation, having a wavelength from 4 to 18 microns, corresponding to the wavelength of energy emitted by visco-elastic material undergoing cyclic stress loads. Such cameras avoid the further complexity of requiring an means to track the blades as they rotate but are more expensive than microbolometer based IR cameras. Wind turbine blade anomalies on an rotating rotor at night, after the blade has come to thermal equilibrium, present in three ways. First, heat may be caused by friction when a defect such as a crack is stressed cyclically by the various forces acting on the blade including the rotating gravity vector, varying wind speed, blade actuation torque, lift from the wind acting of the blade airfoil. This heat flows through to the surface of blade and appears as a hot spot. Defects such as fiber waves and fatigue cracks produce such higher temperature thermal indications.

The cyclic forces acting on the blade also generates heat due to the visco-elastic properties of the composite materials. Other types of defects such as delaminations in the composite sandwich construction of the blade can block the flow of heat from deeper within the blade. Such defects appear dark, as the surface temperature of the blade surface at that location is cooler than the adjacent areas.

Figure 7:
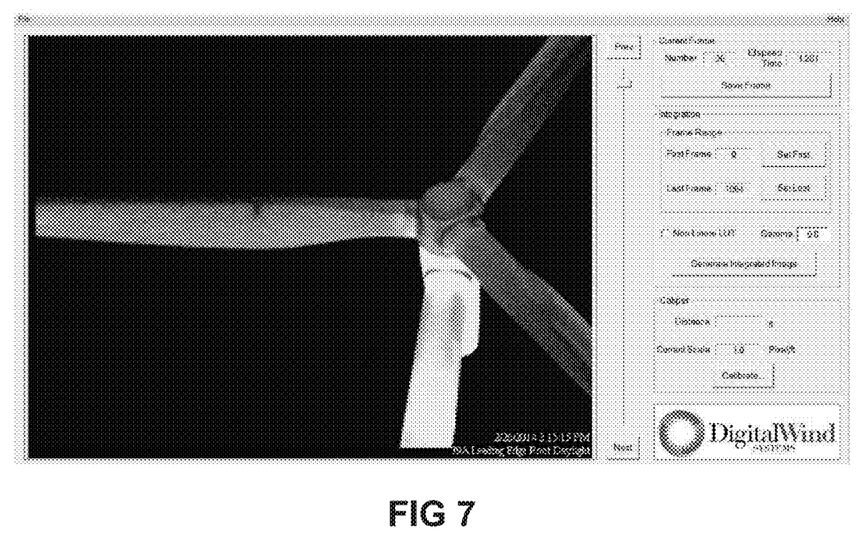
FIG. 7 is a screenshot of a display image generated by the image processing computer showing a thermal image of the high pressure side of an operating wind turbine rotator with a video frame selected with the blade positioned horizontally blade showing a dark defect during nightime.

FIG. 7 is a screenshot of a display image generated by the image processing computer showing a thermal image of the high pressure side of an operating wind turbine rotator with a video frame selected with the blade positioned horizontally blade showing a dark defect. This image was taken at night after the blade has come to thermal equilibrium from the effects of solar heating during the day. This delamination type defect is blocking the heat generated deeper in the blade and preventing it from reaching the surface. The camera used to record this image has a fast integration time of 0.001 seconds. Another defect type that appears dark is a perforation of the blade shells, the two bonded halves that comprise the blade.

Air inside the blade is pressurized by the centripedal acceleration due to the rotator rotation. Compressed air flowing through holes cools the material adjacent to such holes. The step of imaging the wind turbine blade may thus be performed while the turbine is rotating and compressing the air within an open cavity inside a hollow turbine blade and causing an inflow of outside ambient air into the cavity. The air cools the composite material within or around defects where it escapes through breaches of blade shell. Other defects that allow material to be partially supported at the surfaces may be cooled by cool ambient air flowing over the blade. Many of these defect types are caused by lightning strikes, transportation damage with through shell cracks and fatigue cracks.

The IR camera may be advantageously mounted on appropriate vehicles to maneuver through the wind farm to test each turbine. Using a remote control pan/tilt mechanism to steer the camera, mounting on the roof of a truck or car greatly increases testing throughput. A GPS enabled helicopter flying a programmed route can reach all of the best test locations for a given wind direction and rotor orientation. In practice 20 towers or more may be tested in one night. The IR camera can also be mounted on a boat for offshore turbine inspections.

Figure 8:
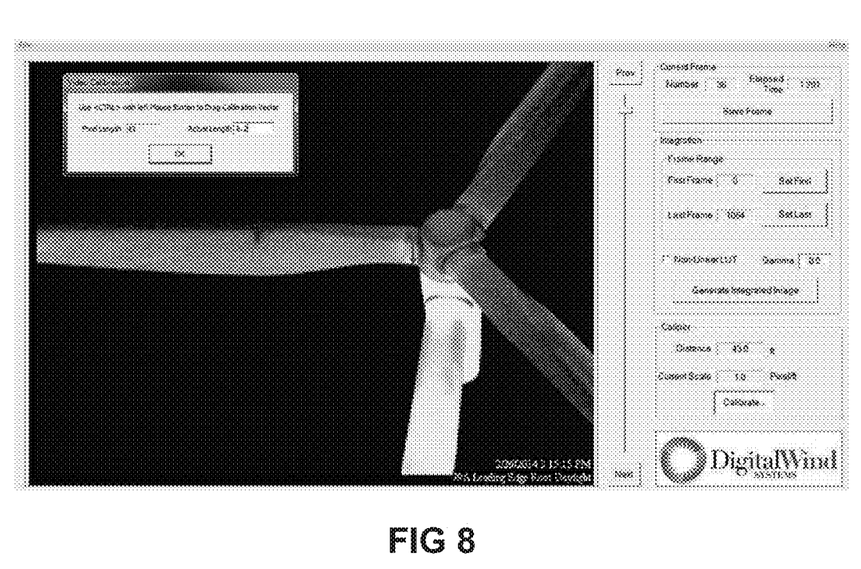
FIG. 8 is a screenshot of a display image generated by the image processing computer showing the use of a caliber overlay function to mark on the digital image the width or diameter of the cylindrical root end of a blade.

The dimensions and location of this defect indication need to be determined to allow proper evaluation and maintenance decisions. FIG. 8 shows how a known distance can be defined on a still IR image of the blade. Here the diameter of the blade root end, known to be 6.2 feet is defined by clicking on one side of the blade root and dragging the measurement line across the image to the opposite side of the blade root, hence defining the diameter of the blade root or a reference line.

Figure 9:
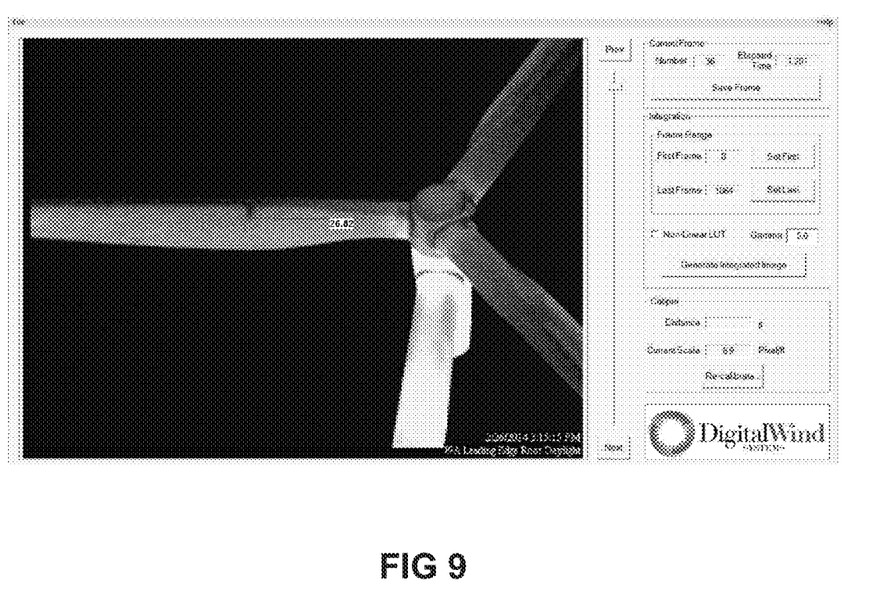
FIG. 9 is a screenshot of a display image generated by the image processing computer showing the use of the caliper overlay function to determine a distance between the blade root end and the black indication of a defect in a wind turbine blade.

The number of pixels in the image that comprise this line are counted to determine the image scale in unites of pixels per unit distance on the image of the blade. The image scale is accurate for all areas of the image of the blade at the same distance from the IR camera as the line segment defining the blade root diameter. The location of the defect with respect to a known datum such as the blade root end can then be measured as shown in FIG. 9. The computer mouses is used to move the cursor to the blade root, where a left click anchors a line at the datum which is then dragged across the image to the defects indications. So long as the line is moved across areas of the blade that are substantially equidistant from the IR camera as the defined reference line, the pixel count divided by the image scale will yield the distance of the defect to the datum.

Figure 10:
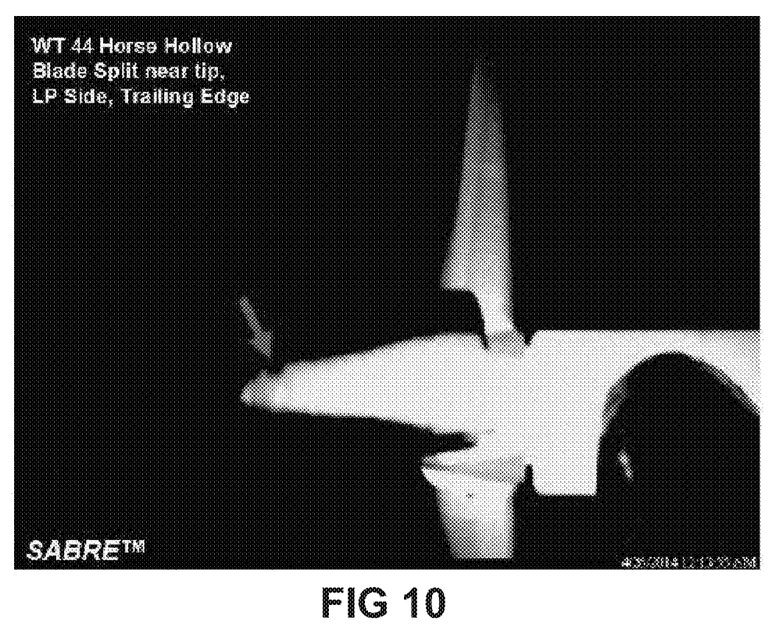
FIG. 10 is an infrared image showing a flaw in a wind turbine blade near the tip of the blade.

Using the high speed IR camera images of blade tip defects, as shown in FIG. 10 are easily detected with sufficient resolution to enable sizing and determination of location, inspite of the faster than 250 ft. per second speed.

Figure 11:
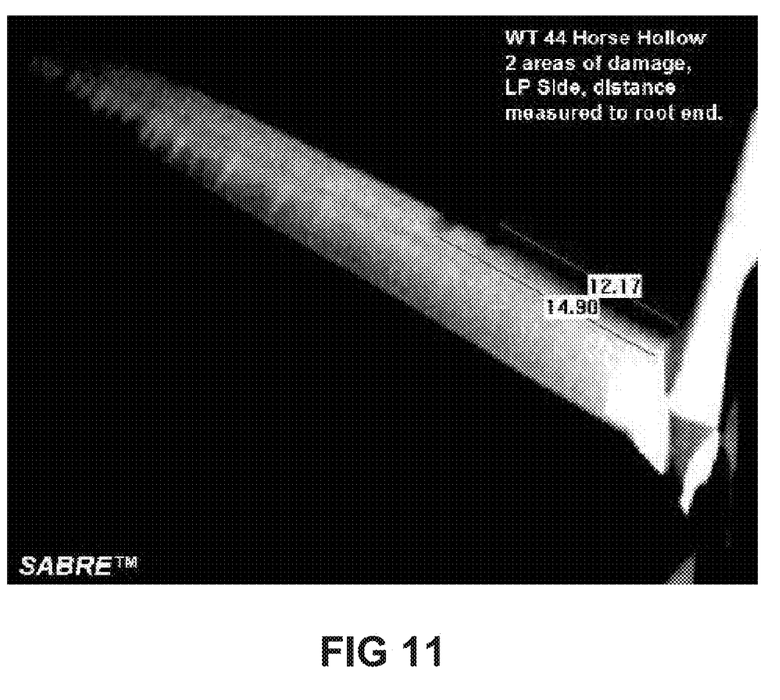
FIG. 11 is an infrared image showing the caliper overlay function being used to measure the location of two areas of damage on a wind turbine blade with respect to the blade root end.

FIG. 11 Shows how two defect indications near the blade root end can be measured using a caliper overlay function.

Digital thermal and photography images are formed by focusing electromagnetic energy with a lens onto a flat sensor comprised of energy sensitive elements or pixels positioned in generally a rectangular array for example 600 horizontal by 420 vertical. As with any image of an object, the image scale, measured in pixels per unit distance on the surface of the object, changes continuously over the field of view as the angle θ between the camera lens and the position of each imaged point on the target changes. For a large flat object with the camera pointed straight on, the line from the center of the camera lens to the target is the shortest distance and the image scale will be largest value. As you move to an edge of the field of view, the angle and distance increase and the image scale decreases.

Figure 12:
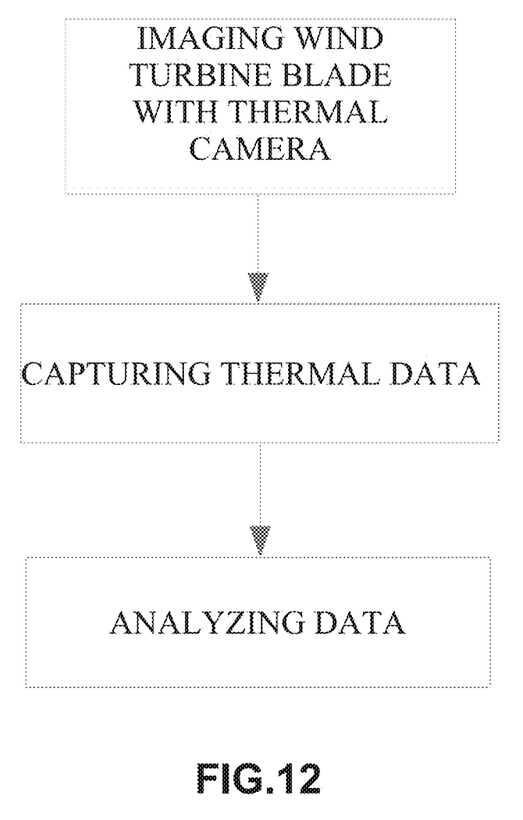
FIG. 12 is a flowchart depicting a method according to a preferred embodiment of the invention.

FIG. 12 shows a preferred method. Objects in the field in a digital image may be measured with respect to other objects of features in the image. First, a the digital image must be calibrated by counting the number of pixels in a line segment that cross and ends at the extremes of a feature of known dimension, located at approximately the same distance from the camera to the feature desired to be measured. The number of pixels counted divided by the features know dimension gives the image scale at that location in pixels/ unit of measure (ft. or meters). Other features or objects can then be measured by counting pixels for either their length or wide or distance from a known datum, if in the field of view, the dimension being the pixel count dived by the image scale.

For wind turbine generators we can select a calibration feature in the digital image that changes apparent width with changes in distance but does not change if the viewing angle changes, giving a more reliable measurement. One example of such an object is a sphere, whose diameter changes with distance, but not with the viewing angle. A cylinder is another example. The root end of wind turbine blades are cylindrical where they attached to the pitch bearing in the hub. Regardless of the blade pitch or the viewing angle from the ground the blade root end diameter can be used to calibrate the image scale of a wind turbine blade and then allow measurement of other features at the same approximate distance.

Another area of known dimension could be the diameter of the tower at the base of the nacelle or at a visible weld joint. Due to the increased thickness of steel at the tower joint welds, these joints retain heat from the sun and remain visible with infrared cameras during most of the night, when thermal inspection of wind turbine blades is best due to washout of defects with thermal emissions. The known dimensions at the blade roots or at tower welds may be used to calibrate the image scale.

The imaging of the area of known dimension could be done using digital thermography, photography or any other passive or active imaging technique. Software is then used to determine an image scale in units of pixels/ft., pixels/ meter or any other scale of pixels to length. Pixel counting is then used to determine a dimension calibrated in pixels of the size and/or area of the indication. This will permit the software to comparatively determine the dimensions of other features or objects, such as anomalies, that are located at approximately the same distance. The dimensions of such features or anomalies may then be converted back to a conventional dimensional measurement, such feet, meters or other units of length. The imaging software may then integrate dimensional measurements to determine the surface area of the feature or anomaly.

A video image of root end of the blade and blade hub may be recorded continuously with a video camera and synchronized with video frames from a thermal camera imaging the blade for anomalies using at least one of GPOS timing signals, wireless signals or other means in order to identify blade serial numbers or the rotor lift lugs, thereby identifying the blade positions of specific blades with anomalies or features of interest.

Such imaging may be conducted with the wind turbine blade at multiple radial angles of rotation in order to generate an image scale template that corrects for image distortion over the field of view of the digital image as the wind turbine blade rotates. The imaging may be performed as the wind turbine blade rotates, so it is not necessary to immobilize the wind turbine blade or take the unit off-line during the inspection process. With the blade oriented horizontally, the angle of the arc subtended by a defect indication on the blade in the image is relatively small, so the error in sizing and locating the the defect is relatively small. Images where the blade is pointing at angles other than horizontally, have an image scale much more distorted by changes in the distance from the IR camera to points on the blade. If the blade is pointing down, the distance from the camera to the blade tip is approximately equal half the height of the tower. The image scale at the blade tip would be twice the value for the image scale at the root and defect measurements would be twice the actual size.

A sequence of digital thermal images or photographic may be played back, frame by frame to allow the analyst the ability to select frames with optimal image quality for the definition of the boundaries of an anomaly. Image measurement tools that measure each pixel value along a line through a defect indication can be programmed to measure the signal to noise ratio which may be defined as the pixel values for the area adjacent to the defect squared divided by the pixel values for the defect indication squared. Such a tool, among many known to those skilled in the art of image processing may be used to quantitatively select the image with the best image quality.

The field operator may image the wind turbine blade in position segments in order to capture a sequence of multiple images of all three blades at least once as they pass through the camera field of view. This may be followed by a rotation of the camera on its mount to capture the next blade segment in order to image a sequence of multiple images of all three blades at least once as they pass through the camera field and so forth until images of the entire blade are captured. In other words, segments broken up by length along the longitudinal axis of the blade, are scanned incrementally from the inside out as the blades rotate.

The analyst reviewing the frame by frame sequence over the full blade length may use an image scale with a distance correction factor to obtain accurate measurements.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of remotely inspecting a rotating wind turbine blade in situ, comprising:
   imaging a wind turbine blade with a thermal imaging camera while the blade is rotating and undergoing cyclic load due to gravity and variations in wind loads and producing thermoelastic emissions, and when the wind turbine blade has substantially reached thermal equilibrium with ambient air alter sunset;
   capturing thermal imaging data; and
   analyzing the thermal imaging data to identify atypical thermal patterns indicative of a flaw in the wind turbine blade.

2. A method of remotely inspecting a rotating wind turbine blade according to claim 1, where the step of imaging the wind turbine blade is performed while the turbine is rotating and compressing the air within an open cavity inside a hollow turbine blade and causing an inflow of outside ambient air into the cavity.

3. A method of remotely inspecting a rotating wind turbine blade according to claim 1, wherein the thermal camera is mounted on a remotely controlled pan/tilt mechanism located on a vehicle.

4. A method of remotely inspecting a rotating wind turbine blade according to claim 1, wherein a video image of root end of the blade and blade hub is recorded continuously with a video camera and synchronized with video frames from a thermal camera imaging the blade for anomalies using at least one of GPOS timing signals, wireless signals or other means in order to identify blade serial numbers or rotor lift lugs, thereby identifying the blade positions of specific blades with anomalies or features of interest.

5. A method of remotely inspecting a rotating wind turbine blade according to claim 1, wherein the atypical thermal patterns are indicative of at least one of frictional heating and aerodynamic cooling of a composite material proximate to a flaw.

6. A method of remotely inspecting a rotating wind turbine blade according to claim 5, wherein the flaw is at least one of a latent manufacturing defect, delamination and crushing damage to a shell of the blade.

7. A method of remotely inspecting a rotating wind turbine blade according to claim 1, wherein the step of imaging the wind turbine blade includes acquiring a continuous sequence of images of a blade as the wind turbine blade passes through a field of view of the thermal imaging camera and analyzing the sequence of images frame by frame to identify atypical thermal patterns indicative of a flaw.

8. A method of remotely inspecting a rotating wind turbine blade according to claim 7, further comprising a step of recording the images and creating a composite image of a selection of sequential blade images with a pixel gray scale value peak-store program to track the motion of the source of thermal emissions to distinguish between an actual thermal emitting area on the blade from unrelated thermal effects or reflections from heat emitters not on the blade itself.

9. A method of remotely inspecting a rotating wind turbine blade according to claim 8, wherein a single image or a continuous series of images of each blade is recorded as it passes through the field of view of the thermal camera, the thermal radiation being directed to the camera having an integration time, t, last enough to reduce a degrading effects of blade rotation creating an image without apparent motion smearing at the blade tip, ranging from 0.001 to 100 milliseconds but ideally, t seconds=$\tau/\pi D$, where D is the diameter of a turbine rotor and $\tau$ is the rotation period of the rotor in seconds.

10. A method of remotely inspecting a rotating wind turbine blade according to claim 1, wherein the thermal camera is mounted to an aerial vehicle.

11. A method of remotely inspecting a rotating wind turbine blade according to claim 10, wherein the aerial vehicle is unmanned.

12. A method of remotely inspecting a rotating wind turbine blade according to claim 11, wherein the unmanned aerial vehicle is flown in a computer controlled flight-plan with GPS to capture thermal images of all relevant sides of the wind turbine blades as they rotate.

13. A method of remotely inspecting a rotating wind turbine blade according to claim 1, further comprising a calibration step wherein an object of known dimension is defined and measured in the image and a number of pixels in this measurement is obtained yielding the image scale, in a direction measured, in pixels per unit length, allowing distance between features or object to be measured.

14. A method of remotely inspecting a rotating wind turbine blade according to claim 13, wherein the object of know dimension is defined and measured in multiple images with the blade positioned at multiple radial angles and an image scale template is generated to correct image distortion and allow accurate distances between features or objects.

* * * * *